United States Patent
Lo

[19]

[11] Patent Number: 5,881,744
[45] Date of Patent: Mar. 16, 1999

[54] DENTAL FLOSSER HAVING A SUBSTANTIALLY E-SHAPED HOLLOW CASING

[76] Inventor: Chen-Wan Lo, P.O. Box 55-175, Taichung, Taiwan

[21] Appl. No.: 958,616

[22] Filed: Oct. 27, 1997

[51] Int. Cl.⁶ .................................................. A61C 15/00
[52] U.S. Cl. .......................................................... 132/325
[58] Field of Search .................................. 132/323, 324, 132/325, 326, 327

[56] References Cited

U.S. PATENT DOCUMENTS

| | | | |
|---|---|---|---|
| 2,217,917 | 10/1940 | Munro | 132/326 |
| 2,544,276 | 3/1951 | Ness | 132/326 |
| 3,746,017 | 7/1973 | Casselman | 132/325 |
| 4,660,584 | 4/1987 | Wofford | 132/325 |
| 4,936,326 | 6/1990 | Eckroat | 132/326 |
| 5,762,078 | 6/1998 | Zebuhr | 132/323 |

Primary Examiner—Todd E. Manahan
Assistant Examiner—Eduardo C. Robert

[57] ABSTRACT

A dental flosser for cleaning the spaces between the teeth is provided. The dental flosser includes a hollow interior casing of roughly E-section having a narrow end and a wide end, a first and a second support for supporting in proper tense of a segment of the floss, a first receiving space for receiving a coiled up floss, a L-shaped second receiving space for receiving a cutting unit, an enlarged circular interior abutting a rectangular interior inside the second support in addition with a pair of accesses for rotatably engaging a rotatable abutment therein. A segment of floss winds on a plurality of first posts and the top of the abutment and engaged with a plurality of second slotted posts inside the narrow end of the casing, and then drawn out from the first support and wind in a slot at, lower end of the abutment, inside the second support for rotatably adjusting the proper tense of the floss. A clip-on cap covers the narrow end of the casing for preventing the floss from stained with external contaminations.

7 Claims, 7 Drawing Sheets

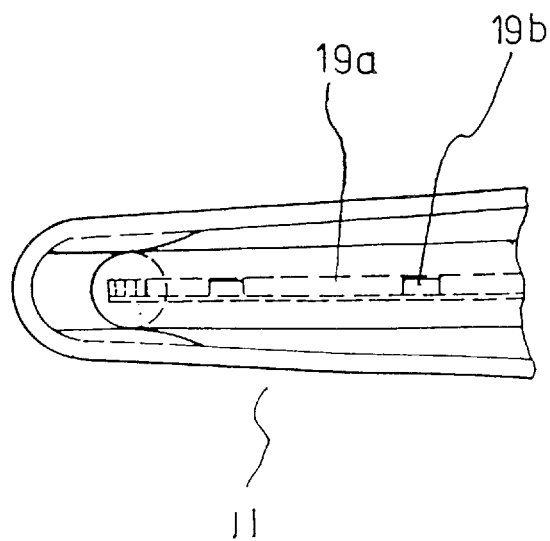
F I G.7
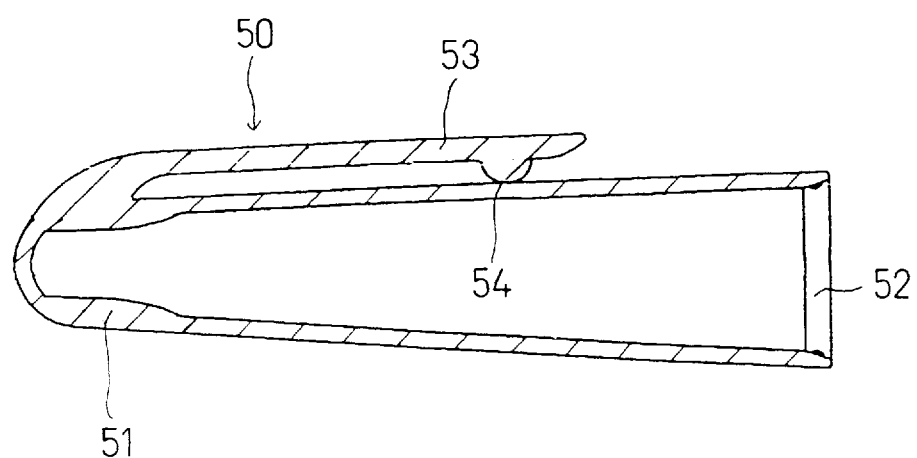
F I G.8

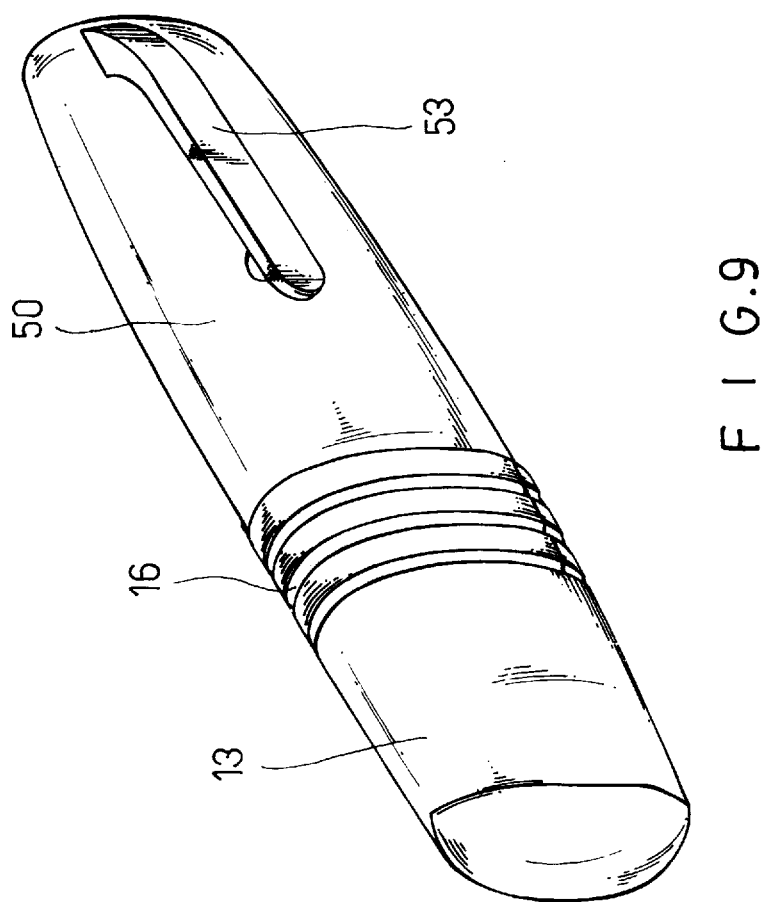

DENTAL FLOSSER HAVING A SUBSTANTIALLY E-SHAPED HOLLOW CASING

BACKGROUND OF THE INVENTION

The present invention relates to dental apparatus and more particularly to a structure improved dental flosser which includes a rotatable abutment, a cutting unit and a clip-on cap so that the tension of the floss is adjustable, the used segment of the floss is cutaway and the floss is kept from external contamination.

The dental flosser becomes more popular than the toothpick in the modern market because it protects the enamel surface of the teeth. FIG. 1 shows an original type of the dental flosser which is composed of a pair of parallel supports 1 and 2, a handle 3 and a segment of floss 4 tensionally secured between the support 1 and 2. So that the users grip the handle 3 and clean the spaces between their teeth. This dental flosser is usually sold in gross package. Each time, the user picks one of them and casts away after it is used so as to waste materials.

FIG. 2 shows an improved dental flosser which comprises a hollow elongate body, a pair of supports 5 parallel projected from a narrow end including a longitudinal slot 6 relative to the body in their free ends, a retaining rod 7 abutting the foot of the inner support 5, a recess 8 in an under side wall and a roller 9 integrating with a ratchet gear rotatably disposed in a wide end of the body for winding the floss thereon. In practice, the floss is drawn out through the recess 8 and abuts on the under side of the body and then secures to the retaining rod 7 after passing through the slots 6 of the supports 5 respectively. The floss is then tensioned by a counterclockwise rotation of the roller 9 so that the ratchet gear is checked from clockwise rotation. This type of dental flosser has an advantage of repeated application. However, it has also several disadvantages set forth as follows:

a) the tension of the floss between the supports 5 is unadjustable so that if the floss is too tense, it will hurt the gum of the teeth, b) for preventing the floss from breakaway, the floss adapted to this type of dental flosser must be rather thick so that a thick floss is difficult to insert into the spaces between the teeth, unless it damages the enamel surface of the teeth, and c) a great segment of floss exposed to the outside of the body oughts to be stained with the external contaminations.

The present invention is arisen to militate and/or obviate the aforediscussed disadvantages and provides a qualified dental flosser to the users.

SUMMARY OF THE PRESENT INVENTION

The present invention has a main object to provide an improved dental flosser which includes an adjustable abutment which is rotatable for providing desired tension of the floss to the users.

Another object of the present invention is to provide an improved dental flosser which receives greatly the floss inside the body for preventing the floss from stained with external contamination.

Still another object of the present invention is to provide an improved dental flosser which includes a cutting unit which can readily cut off the used segment of the floss in order to keep the floss to be sanitary.

Further object of the present invention is to provide an improved dental flosser which includes a clip-on cap which not only protects the floss and other elements from external contamination but also facilitates the dental flosser to be portable in the user's pocket.

The present invention will become more fully understood by reference to the following detailed description thereof when read in conjunction with the attached drawings.

BRIEF DESCRIPTION OF THE DRAWINGS

FIG. 7 is a sectional view to show an alternative embodiment of the present invention, FIG. 8 is a sectional view of the clip-on cap, and FIG. 9 is a perspective view to show an outlook of the dental flosser according to the present invention.

DETAILED DESCRIPTION OF THE PREFERRED EMBODIMENT

Figure 1:
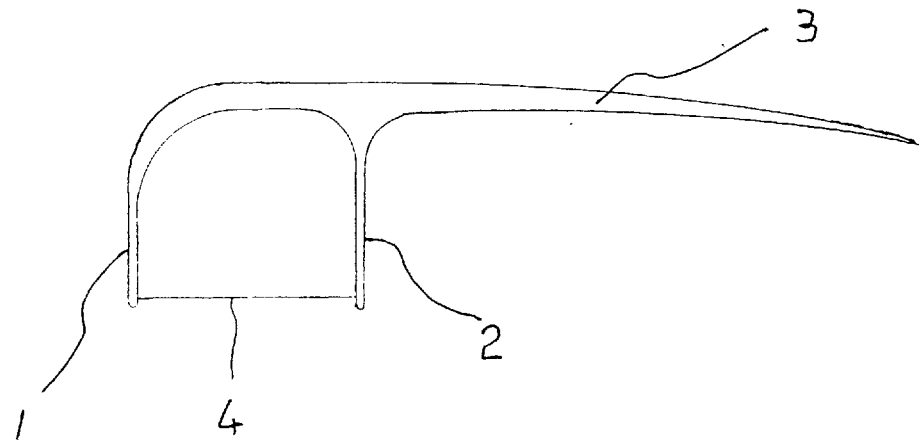
FIGS. 1 and 2 are the side views to show the dental flossers of the prior art.
Figure 2:
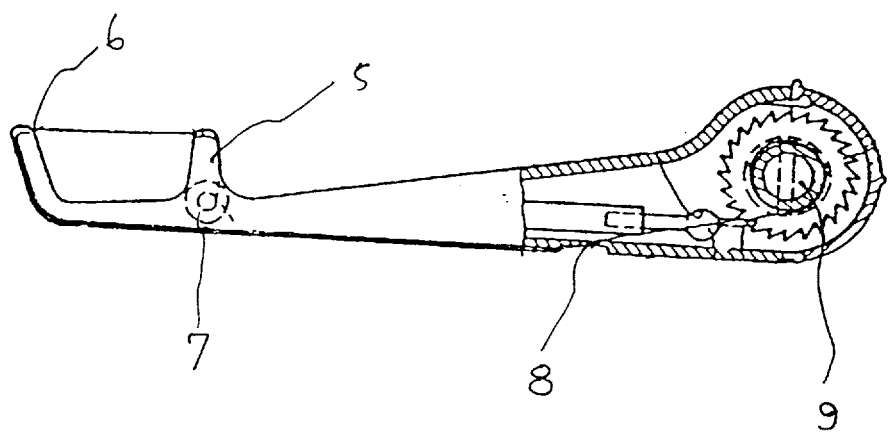
Figure 3:
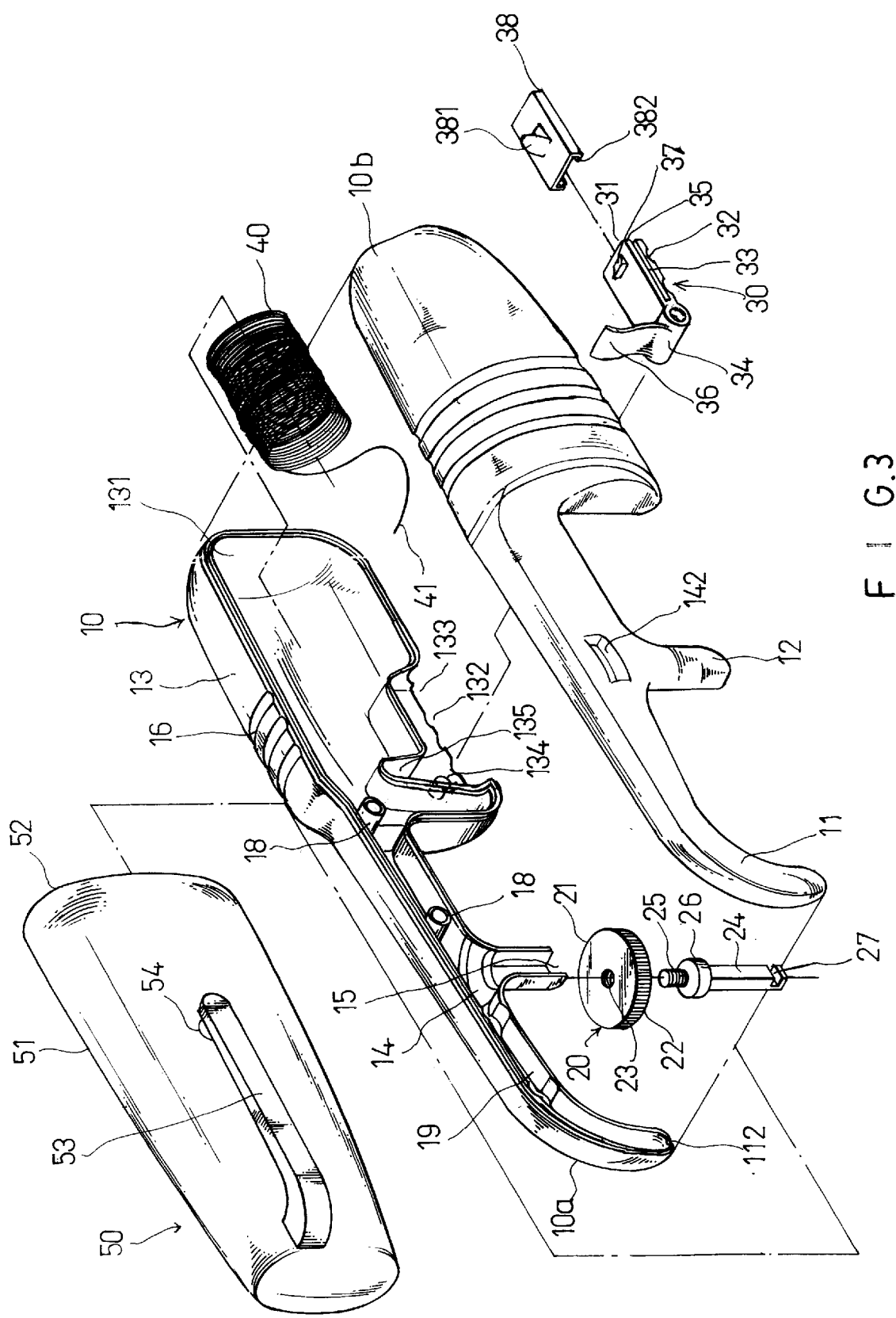
FIG. 3 is an exploded perspective view to show a preferred embodiment of the present invention.

With reference to FIG. 3, the dental flosser of the present invention comprises a hollow interior casing 10 of a generally E-shaped section combined with a pair of symmetrical halves 10a and 10b and including a wide end and a narrow end, a rotatable abutment 20, a cutting unit 30, a coiled up floss 40 and a clip-on cap 50.

Figure 4:
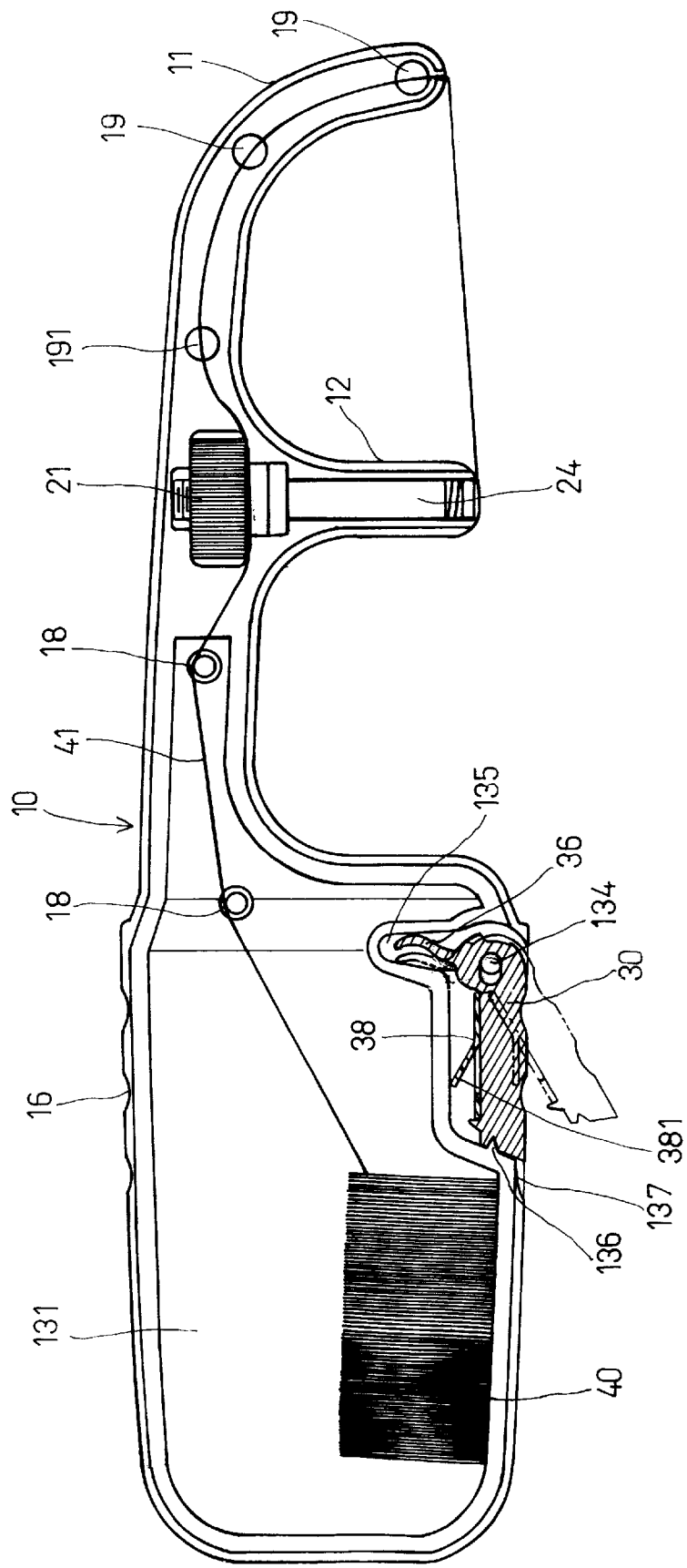
FIGS. 4 to 6 are the side views to show an assembled dental flosser of FIG. 3 and the operation of the cutting unit.

Each half 10a and 10b of the casing 10 includes a first support 11 which is the narrow end of the casing 10 and has a recess 112 in the distal for passing through the floss, a second support 12 extended downward from a middle between the first support 11 and the wide end 13 including an elongate circular interior 14 on the top abutting a rectangular interior 15 in the lower portion opening to the outside of the second support 12 for engagement of the rotatable abutment 20, a pair of accesses 142 laterally formed in the side walls of the narrow end above the rectangular interior 15 and engageable with the gear 21 of the rotatable abutment 20, a plurality of first posts and second slotted posts 18 and 19 transversely disposed spaced apart from the inner surface of the side wall of the narrow and wide ends along the longitudinal length thereof for supporting the floss and a grooved portion 16 formed on the upper outer surface of the wide end 13 for facilitating the user to grip the dental flosser in application. The wide end 13 further includes a hollow interior 131 for receiving the coiled up floss 40 and an opened roughly L-shaped receiving space 132 engageable with the cutting unit 30. The L-shaped receiving space 132 includes a rectangular opening 133, an axial pin 134 projected transversely from an appropriate inner wall, a narrower vertical portion 135, a retaining protrusion 136 transversely formed on one end opposite to the axial pin 134 and a groove 137 formed in an outer surface of the wide end 13 adjacent the protrusion 136 (as shown in FIG. 4). The rotatable abutment 20 comprises a circular wheel 21 rotatably engageable into the circular interior 14 and accessible from the accesses 142 and including a splined outer periphery 22 and a threaded central bore 23, a rectangular rod 24 slidably engaged into the rectangular lower interior of the second support 12 including a threaded cylinder upper end 25 made in registry with the central bore 23, a flange 26 extended outward from under the cylinder upper end 25 and a slot 27 laterally formed adjacent the lower end thereof.

The cutting unit 30 comprises a rectangular seat 31 which is a lip of the L-shaped receiving space 132, a grooved thumbpiece 32 on the under side, a pair of slidable slots 33 formed along the lateral sides, a joint 34 at one end rotatably engageable with the axial pin 134, a snap slot 35 in the other end engageable with the retaining protrusion 136, an elastic plate 36 extended upward from an upper periphery of the joint 34, a wedge means 37 centrally formed on the top of the rectangular seat 31 adjacent one end opposite to the joint 34 and a rectangular blade means 38 including an upwardly slant blade 381 on a top and a pair of engaging flanges 382 of L-shaped section laterally formed on under side slid into the slidable slots 33. When the blade means 38 slides in place into the slots 33, its outward end will be retained by the wedge means 37 and when the cutting unit 30 closes the L-shaped receiving space 132 in a snap fitting, its elastic plate 36 will bias in the narrower vertical portion 135 for reserving resilient energy to eject the cutting unit 30 out of the receiving space 132 (as shown in FIG. 4).

The clip-on cap 50 includes a generally tapered hollow body 51, an opening 52 engageable with the casing 10 and an elastic clip 53 internally formed with the wide end of the body 51 and extended longitudinally along an outer periphery of the body 51 having a dome 54 on the inner side of the free end stopped against the outer surface of the body 51 (as shown in FIGS. 3 and 8).

Figure 5:
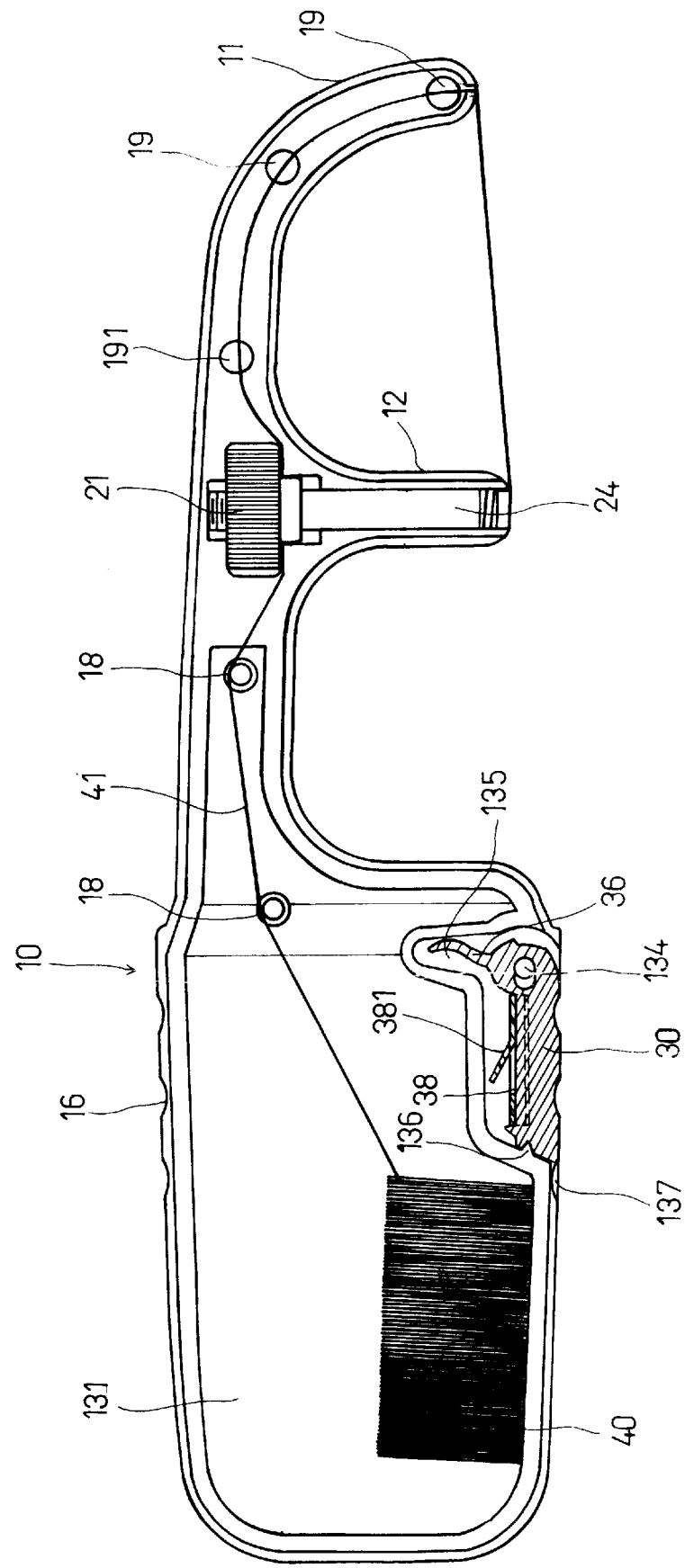
Figure 6:
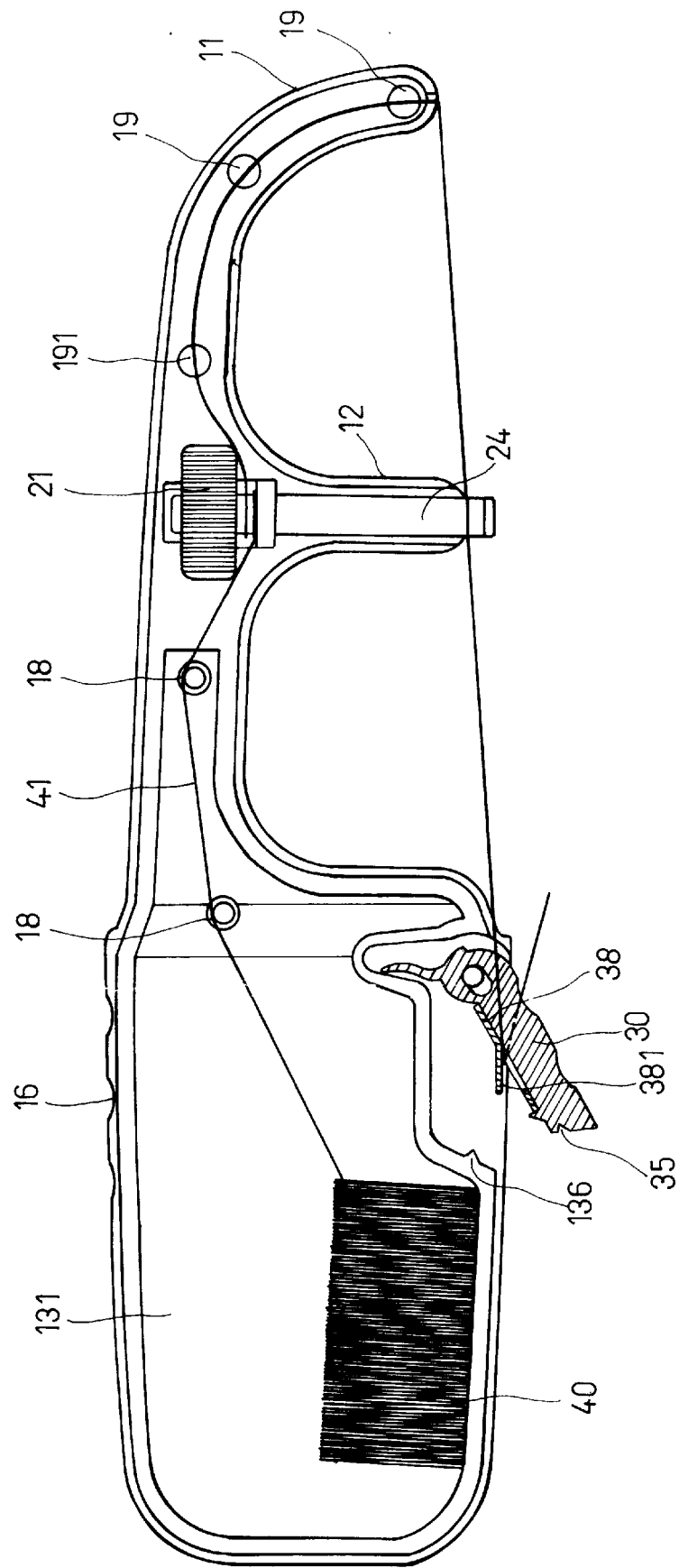

Referring to FIGS. 5 to 6 and FIG. 4 again, when assembly, first dispose the coiled tip floss 40 into the hollow interior 131 and the rotatable abutment 20 in place into the second support 12 as the circular wheel 21 engaged into the circular interior 14 and the access 142 and the threaded cylinder upper end 25 of the rectangular rod 24 partially screwed into the threaded central bore 23, secondly, draw a segment of the floss 41 in appropriate length out of the coiled up floss 40 and wind the floss 41 onto the first posts 18 and the threaded cylinder upper end 25 of the rotatable abutment 20 respectively and then engage the floss 41 respectively into the slotted ends 191 of the second slotted posts 19 and draw the floss 41 out of the first support 11 via the recess 112 and wind the end of the floss 41 into the slot 27 of the rotatably abutment 20, this time, turn about the circular wheel 21 to adjust the proper tension of the floss 41, thirdly, mount the cutting unit 30 in place into the L-shaped receiving space 132 by engaging one end of the joint 34 onto the axial pin 134 and engaging the snap slot 35 with the retaining protrusion 136 in a snap fitting, finally, combine the halves 10a and 10b of the casing 10 together and weld with high frequency.

Generally, this time, the dental flosser of the present invention is in condition ready for use. If wants to replace the used segment of the floss 41, first turn about the circular wheel 21 of the rotatable abutment 20 getting the lower end of the rectangular rod 24 out of the second support 12 so as to unwind the end of the floss 41 from the slot 27, secondly, press the engaging end of the cutting unit 30 so that the elastic plate 36 will eject the engaging end out of the space 132 on its resilient force (as shown in FIG. 6), thirdly, cut off the used segment of the floss 41 on the blade 381 and wind the end of fresh segment of the floss 41 into the slot 27 and turn about the circular wheel 21 simultaneously to contract the lower end of the rectangular rod 24 into the second support 12 and adjust the proper tension of the floss 41, meanwhile, the cutting unit 30 is closed into the L-shaped receiving space 132 in a snap fitting. When the dental flosser of the present invention is not in use, mount the clip-on cap 50 so as to prevent the dental floss from stained with external contaminations and the dental flosser is portable in user's pocket. FIG. 9 shows an outlook of the dental flosser of the present invention. Note that when the flange 26 of the rectangular rod 24 stops against the under side of the circular wheel 21, the floss 41 is clipped and prevented from further movement. Besides, the floss 41 is hidden in the first support 11, it would no longer be contaminated.

Referring to FIG. 7, an alternative embodiment of first support 11a is shown in which the structure and function are mostly similar to the first support 11 described in FIG. 4 and the aforediscussions are applicable in most instance. The change is characterized in that a plurality of semi-cylinder grooves 19a is centrally formed in the inner wall along the axis of first support 11 of the first half 10a instead of the second slotted post 19 adjacent the recess 112 and a plurality of semi-cylinder projections 19b centrally formed spaced apart on the inner wall along the axis of the first support 11 of the second half 10b. Since the diameter of the semi-cylinder projections 19b are smaller than the diameter of the semi-cylinder grooves 19a, so that the semi-cylinder projections 19b are engageable into the semi-cylinder grooves 19a and leave a gap therebetween for permitting the floss 41 going through.

Note that the specification relating to the above embodiment should be construed as exemplary rather than as limitative of the present invention, with many variations and modifications being readily attainable by a person of average skill in the art without departing from the spirit or scope thereof as defined by the appended claims and their legal equivalents.

I claim:

1. A dental flosser comprising:

a substantially E-shaped hollow casing having a wide end and a narrow end formed by a pair of symmetrical halves, said narrow end having a downwardly curved first support with an aperture in a distal end thereof, said wide end having a receiving space for a coiled-up floss, said casing further having a second support extending downwardly between said first support and said wide end, said second support having an enlarged circular interior top and a rectangular interior extending downwardly from said circular interior top to an opening at a distal end thereof, said hollow casing further having a pair of lateral access openings formed therein above said rectangular interior adjacent said enlarged circular top of said second support;

a rotatable abutment engaging said enlarged circular interior top of the second support and extending through said rectangular interior;

a plurality of first posts and slotted second posts disposed within said hollow casing between the narrow and wide ends;

a grooved thumb piece formed on an outer surface of the wide end; and an L-shaped receiving space formed in a lower portion of the wide end having a cutting unit disposed therein for cutting off a segment of used floss;

whereby a segment of the floss drawn from said coiled-up floss is wound about each of said first posts and an upper end of said rotatable abutment, and thereafter passes through said slotted second posts and out through the aperture of said first support and then secured to wound onto a lower end of said rotatable abutment.

2. A dental flosser as recited in claim 1 wherein said rotatable abutment comprises:

a circular wheel rotatably engaged in said enlarged circular interior top of the second support and accessible from said pa, of lateral access openings, said circular wheel having a splined periphery and a threaded central bore; and a rectangular rod slidably disposed within said rectangular interior of the second support with a lower end thereof extending through said opening in the distal end of said second support, said rectangular rod including a threaded cylindrical upper end which is received by the threaded central bore of the circular wheel, a flange beneath the cylindrical upper end for stopping against an underside of the circular wheel, and a lateral slot formed at the lower end of the rectangular rod for securing a segment of floss therein.

3. A dental flosser as recited in claim 1, wherein said L-shaped receiving space includes a rectangular opening, an axial pin projecting transversely from an inner wall of said L-shaped receiving space, a narrower vertical portion and a retaining protrusion transversely formed on an end of said rectangular opening opposite to said axial pin, and a groove formed in an outer surface of said wide end of said casing adjacent the retaining protrusion.

4. A dental flosser as recited in claim 1 wherein said cutting unit includes:

a rectangular seat engaging into said L-shaped receiving space;

a joint at one end of said rectangular seat rotatably engaged with said axial pin;

an elastic plate projecting upwardly from the joint for stopping against an inner wall of said vertical portion;

a snap slot transversely formed in another end of the rectangular seat opposite to the joint;

a wedge means centrally formed on a top of the seat adjacent the snap slot;

a grooved thumb piece formed on an underside of the seat; and a pair of slots transversely extending along two lateral sides of said rectangular seat and which receive a rectangular blade means, said blade means including an upwardly slanted blade on a top with a pair of L-shaped flanges laterally formed on an underside thereof slidably engaging the pair of slots, said blade means being retained on an outward end of said rectangular seat by said wedge means.

5. A dental flosser as recited in claim 1 further including a clip-on cap on the narrow end of said casing, said cap including a hollow tapered body having an opening at one end thereof engageable with the wide end of the casing and a longitudinally extending elastic clip integrally formed with said body.

6. A dental flosser as recited in claim 1 wherein said symmetrical halves of said casing are bonded together by ultra-sonic welding.

7. A dental flosser as recited in claim 1 wherein said first support further includes a plurality of semi-circular grooves formed spaced apart along an inner surface of a side wall made engageable with a plurality of semi-circular protrusions formed spaced apart along an inner surfade of an opposing side wall of said casing.

* * * * *